(12) United States Patent
Maa et al.

(10) Patent No.: US 11,103,612 B2
(45) Date of Patent: Aug. 31, 2021

(54) AIR-FILTERING ANTI-BACTERIAL LIGHTING DEVICE

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 0 days.

(21) Appl. No.: 17/094,567

(22) Filed: Nov. 10, 2020

(65) Prior Publication Data

US 2021/0077653 A1     Mar. 18, 2021

Related U.S. Application Data

(63) Continuation-in-part of application No. 16/180,416, filed on Nov. 5, 2018, now Pat. No. 10,874,762.

(51) Int. Cl.
| | |
|---|---|
| *A61L 9/20* | (2006.01) |
| *B01J 35/00* | (2006.01) |
| *B01D 46/00* | (2006.01) |
| *B01J 21/06* | (2006.01) |
| *B01J 19/12* | (2006.01) |

(52) U.S. Cl.
CPC .......... *A61L 9/205* (2013.01); *B01D 46/0028* (2013.01); *B01J 19/123* (2013.01); *B01J 21/063* (2013.01); *B01J 35/004* (2013.01); *A61L 2209/12* (2013.01); *B01D 2273/30* (2013.01)

(58) Field of Classification Search
CPC .. A61L 9/205; A61L 2209/12; A61L 2209/24; A61L 2202/25; B01J 35/004; B01J 35/0013; B01J 21/063; B01J 23/50; B01J 23/52
See application file for complete search history.

(56) References Cited

U.S. PATENT DOCUMENTS 8,900,518 B2 *  12/2014  Seck ..................... F21V 1/00
                                              422/121

* cited by examiner

*Primary Examiner* — Lessanework Seifu
(74) *Attorney, Agent, or Firm* — Han IP PLLC; Andy M. Han

(57) ABSTRACT

An anti-bacterial lighting device includes a translucent housing, a first light source, a second light source, an air-inflow port, and an air circulation mechanism. The translucent housing is air-permeable and coated with an anti-bacterial photocatalyst on its surface. The first light source is a visible light source emitting a visible light with a spectral power distribution (SPD)>95% in a visible light wavelength range (>400 nm). The second light source is a far-UVC light source emitting a non-visible light with an SPD>90% in a 200 nm~230 nm wavelength range. The lights of the first light source and the second light source shine through the translucent housing and activates the anti-bacterial photocatalyst on the housing. The air circulation mechanism sucks an ambient air into the housing through the air-inflow port and forces the air out through the air-permeable housing.

20 Claims, 4 Drawing Sheets

AIR-FILTERING ANTI-BACTERIAL LIGHTING DEVICE

CROSS-REFERENCE TO RELATED PATENT APPLICATION(S)

The present disclosure is a continuation-in-part (CIP) of U.S. patent application Ser. No. 16/180,416, filed 5 Nov. 2018, the content of which being incorporated by reference in its entirety herein.

BACKGROUND

Technical Field

The present disclosure pertains to the field of lighting devices and, more specifically, proposes an anti-bacterial lighting apparatus.

Description of Related Art

In U.S. patent application Ser. No. 16/180,416, an air-filter anti-bacterial lighting apparatus was introduced. That lighting apparatus comprises one translucent housing, at least one light source, and an air circulation mechanism. The translucent housing may be air-permeable, and it contains at least one air-inflow port. The inside surface of the translucent housing is coated with anti-bacterial photocatalytic film. The at least one lighting is disposed inside the housing. The light originated from the light source shines through the translucent housing, thus illuminating the area around the apparatus. The light also activates the anti-bacterial photocatalytic film on the housing so that it would kill pathogens making contact with it. The air circulation inside the housing sucks the ambient air from outside the housing and forces the air through the air-permeable housing. As the air passing through, the air-permeable housing traps airborne pathogens, and the activated anti-bacterial photocatalytic film would kill the trapped pathogens. The translucent housing serves three purposes: firstly, as a housing to house the light source and the air circulation mechanism; secondly, as an photocatalytic air-filter for filtering airborne pathogens and killing the trapped pathogens; and thirdly, as a lightshade for toning down the light emitted from the light source. Since the light emitted from the light source would come out of the translucent housing, an ultraviolet light (UV) source emitting a light in the 230~280 nm wavelength range cannot be used for such wavelength would cause skin and eye damages to a user. Therefore, that lighting apparatus uses only a visible light source emitting a light in the wavelength range>400 nm, and it pairs the visible light source with a high-density rhombus-shaped anatase-type titanium dioxide ($TiO_2$) which can be activated by visible light.

Recent studies have demonstrated that a far-UVC light within a wavelength range 200~230 nm has the effect of killing bacteria and viruses, but without the side effect of causing skin and eye damages to a user. One such study can be found at https://www.cuimc.columbia.edu/news/far-uvc-light-safely-kills-airborne-coronaviruses. This gives rise the possibility of incorporating a far-UVC light source with a 200 nm-230 nm wavelength range into the lighting apparatus introduced in U.S. patent application Ser. No. 16/180,416. Such arrangement would result in two enhancements to that lighting apparatus. The first enhancement lies in that such far-UVC light source would accelerate the photocatalytic activity of the photocatalytic film coated on the translucent housing, much faster than the photocatalytic activity induced by the visible light wavelength from the visible light source. The second enhancement lies on the fact that such far-UVC light source can disinfect directly the pathogens in the air inside the housing and on the surface of the housing. As a result, the overall disinfection efficiency against airborne pathogens can thus be improved significantly.

SUMMARY

In one aspect, the lighting device comprises one translucent housing, a first light source, a second light source, an air inflow port, and an air circulation mechanism. The translucent housing houses the first light source, the second light source, and the air circulation mechanism. The translucent housing is air-permeable and is coated with an anti-bacterial photocatalyst on its surface. The coating may be on one side or both sides of the housing surface, and the coating may be on the housing surface completely or partially. The first light source is a visible light source emitting a visible light with a spectral power distribution (SPD)>95% in a visible light wavelength range (>400 nm). The second light source is a far-UVC light source emitting a non-visible light with an SPD>90% in a 200 nm~230 nm wavelength range. The first light source and the second light are disposed inside the housing, and their lights shine through the translucent housing and activates the anti-bacterial photocatalyst coated on the housing. Both light sources contribute to the activation of the photocatalyst, thus enhancing the efficiency of the photocatalytic process. The air circulation mechanism sucks an ambient air into the housing through the air-inflow port and forces the air out through the air-permeable housing. The air-permeable translucent housing traps airborne pathogens, and the activated anti-bacterial photocatalyst on the housing disinfects the trapped pathogens. Moreover, the far-UVC light emitted from the second light source has the effect of directly disinfecting the pathogens in the air inside the housing and on the surface of the housing.

The air-permeable translucent housing of the present disclosure serves three functions. Firstly, it severs as a housing to house the light sources and the air circulation mechanism. Secondly, it serves as a light shade to tone down the light emitted from the first light source and to reduce the amount of (invisible) light emitted from the second light source for passing through. Thirdly, it serves as an anti-bacterial air filter for trapping and disinfecting the airborne pathogens.

It is foreseeable to use a frame either inside or outside of the translucent housing to support the housing. However, in some embodiments, the translucent housing is free-standing and requires no frame to house the first light source, the second light source, and the air circulation mechanism.

In some embodiments, the primary ingredient of the anti-bacterial photocatalyst is titanium dioxide ($TiO_2$). In some other embodiments, the primary ingredient is rhombus-shape anatase-type titanium dioxide ($TiO_2$). As shown in U.S. Pat. No. 9,522,384 by Liu L. et al that rhombus-shape anatase-type titanium dioxide has a much higher volume density than the sphere-shape anatase-type titanium dioxide, thus it is more effective in the photocatalytic killing of bacteria and viruses.

In some embodiments, the anti-bacterial photocatalytic film may contain a secondary ingredient made of a metal, such as silver, gold, copper, zinc, or nickel. These metals when embedded in the photocatalyst are known to enhance the photocatalytic activity with visible light. The photocatalyst may contain more than one type of metals for a better photocatalytic effectiveness.

The titanium dioxide is classified as a semiconducting photocatalyst. Recently technology breakthrough has demonstrated that noble metal nanoparticles such as gold (Au) and silver (Ag) are a class of efficient photocatalysts working by mechanisms distinct from those of semiconducting photocatalysts (https://pubs.rsc.org/en/content/articlelanding/2013/gc/c3gc40450a#!divAbtstract). The present disclosure is not limited to the use of semiconducting photocatalysts. In some embodiments, the primary ingredient of the anti-bacterial photocatalytic film is a noble metal nanoparticle such as but not limited to, gold (Au) or sliver (Ag).

In some embodiments, the air circulation mechanism is a fan. It is foreseeable to have more than one fans to increase the airflow.

Since the housing functions as an air filter, the dust will get stuck on the housing surface and gradually blocks the physical contact of the anti-bacterial photocatalyst with the airborne bacteria and viruses, thus reducing the anti-microbial effectiveness of the device. Moreover, the translucent housing will become dirty over time. To overcome these issues, in some embodiments, the housing of the present disclosure is replaceable. It is foreseeable to use a timer tracking the usage of the housing or a sensor detecting the cleanness of the housing for reminding the user to replace the housing when necessary.

In some embodiment, the housing may be made of non-woven fabric. There are at least four advantages of using non-woven fabric as the material for air filter. Firstly, it is easier to control the air permeation rate through the manufacturing process of the non-woven air filter. Secondly, it is easier to apply the anti-bacterial photocatalyst on a non-woven fabric because it has plenty of spores for absorbing the photocatalytic particles. Thirdly, the overall production cost is low with non-woven fabric air filter. Lastly, the translucency of the non-woven fabric can be fine-tuned during the manufacturing process.

In some embodiments, the first light source comprises one or more light emitting diodes (LEDs). In some other embodiments, the first light source comprises one or more organic LEDs (OLEDs). In some other embodiments, the second light source comprises one or more LEDs.

A far-UVC light source can disinfect the pathogens in the air and on the surface, without working in conjunction with a photocatalyst. In another aspect, the lighting device of the present disclosure comprises one translucent housing, a first light source, a second light source, an air inflow port, and an air circulation mechanism. The translucent housing houses the first light source, the second light source, and the air circulation mechanism. The translucent housing is air-permeable. The first light source is a visible light source emitting a visible light with a spectral power distribution (SPD)>95% in a visible light wavelength range (>400 nm). The second light source is a far-UVC light source emitting a non-visible light with an SPD>90% in a 200 nm~230 nm wavelength range. The first light source and the second light are disposed inside the housing, and their lights shine through the translucent housing. The air circulation mechanism sucks an ambient air into the housing through the air-inflow port and forces the air out through the air-permeable housing. The air-permeable translucent housing traps airborne pathogens. Moreover, the far-UVC light emitted from the second light source has the effect of directly disinfecting the pathogens in the air inside the housing and on the surface of the housing.

In some embodiments, the translucent housing is free-standing and requires no frame to house the first light source, the second light source, and the air circulation mechanism.

In some embodiments, the air circulation mechanism is a fan. It is foreseeable to have more than one fans to increase the airflow.

In some embodiments, the housing of the present disclosure is replaceable. And in some embodiment, the housing may be made of non-woven fabric.

In some embodiments, the first light source comprises one or more light emitting diodes (LEDs). In some other embodiments, the first light source comprises one or more organic LEDs (OLEDs). In some other embodiments, the second light source comprises one or more LEDs.

BRIEF DESCRIPTION OF THE DRAWINGS

The accompanying drawings are included to aid further understanding of the present disclosure, and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting devices having different form factors.

The present disclosure discloses an anti-bacterial lighting device that has one translucent housing, two light sources, an air inlet port, and an air circulation mechanism. The translucent housing is air-permeable and coated with an anti-bacterial photocatalyst on its surface. The first light source is a visible light source emitting a visible light with a spectral power distribution (SPD)>95% in a visible light wavelength range (>400 nm). The second light source is a far-UVC light source emitting a non-visible light with an SPD>90% in a 200 nm~230 nm wavelength range. The lights of the first light source and the second light source shine through the translucent housing and activates the anti-bacterial photocatalyst on the housing. The air circulation mechanism sucks an ambient air into the housing through the air-inflow port and forces the air out through the air-permeable housing. The air-permeable translucent housing traps airborne pathogens, and the activated anti-bacterial photocatalyst on the housing disinfects the trapped pathogens. Moreover, the far UV light emitted from the second light source disinfects directly the pathogens in the air and on the surface of the translucent housing.

Example Implementations

Figure 1:
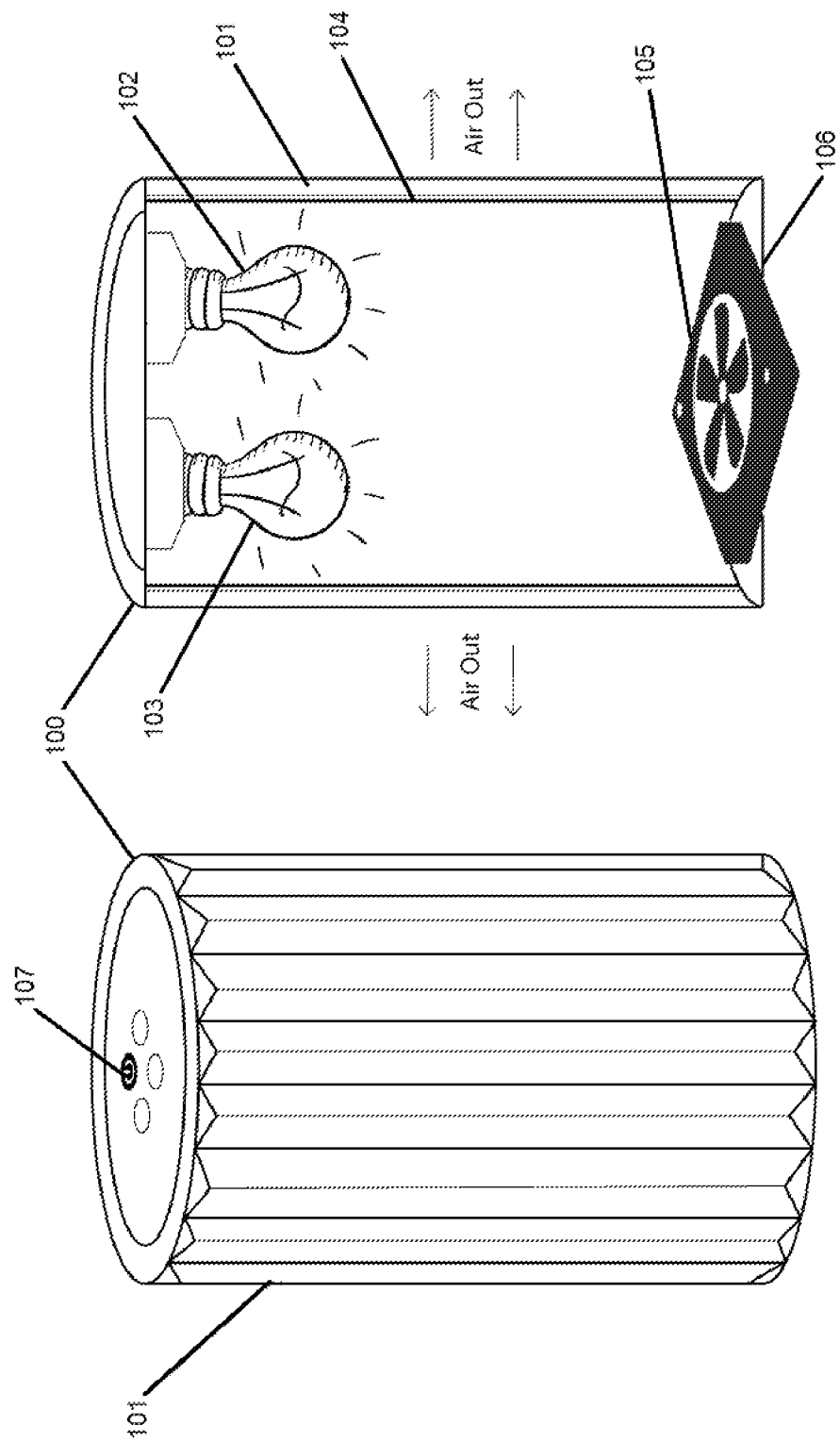
FIG. 1 schematically depicts a diagram of anti-bacterial lighting fixture with a cylindrical housing.

FIG. 1 is an embodiment of the lighting device of the present disclosure in a form of a cylindrical lighting fixture 100. The housing 101 houses the first light source 102, the second light source 103, and a fan 105. The fan 105 is disposed at the air inlet port 106. The translucent housing 101 is air-permeable and is coated with an anti-bacterial photocatalyst 104 on its surface. The first light source 102 is a visible light source emitting a visible light with a spectral power distribution (SPD)>95% in a visible light wavelength range (>400 nm). The second light source 103 is a far-UVC light source emitting a non-visible light with an SPD>90% in a 200 nm~230 nm wavelength range. The first light source 102 and the second light source 103 are disposed inside the housing 101, and their lights shine through the translucent housing 101 and activate the anti-bacterial photocatalyst 104 coated on the housing. The fan 105 sucks an ambient air into the housing 101 through the air-inflow port 106, and it forces the air out through the air-permeable housing 101. The air-permeable translucent housing 101 traps airborne pathogens, and the activated anti-bacterial photocatalyst 104 on the housing disinfects the trapped pathogens. Additionally, the far-UVC light emitted from the second lighting source 103 also disinfects the pathogens in the air inside the housing 101 and on the surface of the housing.

The translucent housing 101 is free-standing and requires no frame to house the first light source 102, the second light source 103, and the fan 105. The primary ingredient of the anti-bacterial photocatalyst 104 is rhombus-shaped anatase-type titanium dioxide ($TiO_2$). The anti-bacterial photocatalyst 104 further include nano silver particles as the secondary photocatalytic ingredient. Though not shown explicitly in FIG. 1, the housing 101 can be removed for replacement when it becomes dirty. The housing 101 is made of non-woven fabric.

Figure 2:
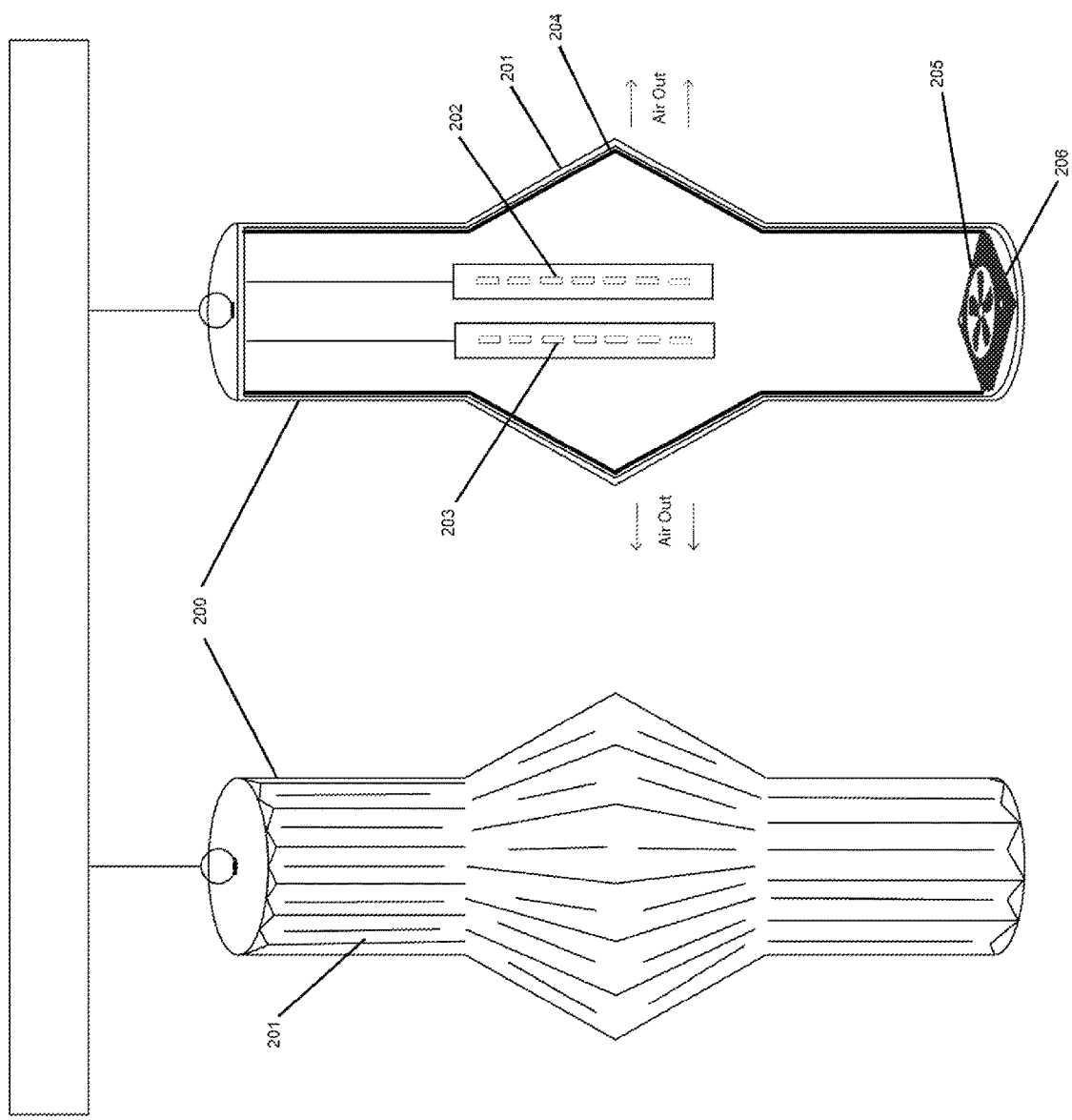
FIG. 2 schematically depicts a diagram of an anti-bacterial lantern fixture.

FIG. 2 is an embodiment of the lighting device of the present disclosure in a form of a lantern fixture 200. The housing 201 houses the first light source 202, the second light source 203, and a fan 205. The fan 205 is disposed at the air inlet port 206. The translucent housing 201 is air-permeable and is coated with an anti-bacterial photocatalyst 204 on its surface. The first light source 202 is a visible light source, comprising multiple LEDs and emitting a visible light with a spectral power distribution (SPD)>95% in a visible light wavelength range (>400 nm). The second light source 203 is a far-UVC light source, comprising multiple LEDs and emitting a non-visible light with an SPD>90% in a 200 nm~230 nm wavelength range. Both light sources 202, 203 are disposed inside the housing 201, and their lights activate the anti-bacterial photocatalyst 204 coated on the housing. The fan 206 sucks an ambient air into the housing 201 through the air-inflow port 206, and it forces the air out through the air-permeable housing 201. The air-permeable translucent housing 201 traps airborne pathogens, and the activated anti-bacterial photocatalyst 204 on the housing disinfects the trapped pathogens. Additionally, the far-UVC light emitted from the second lighting source 103 also disinfects the pathogens in the air inside the housing 101 and on the surface of the housing. Though not shown explicitly in FIG. 2, the housing 201 can be removed for replacement when it becomes dirty.

Figure 3:
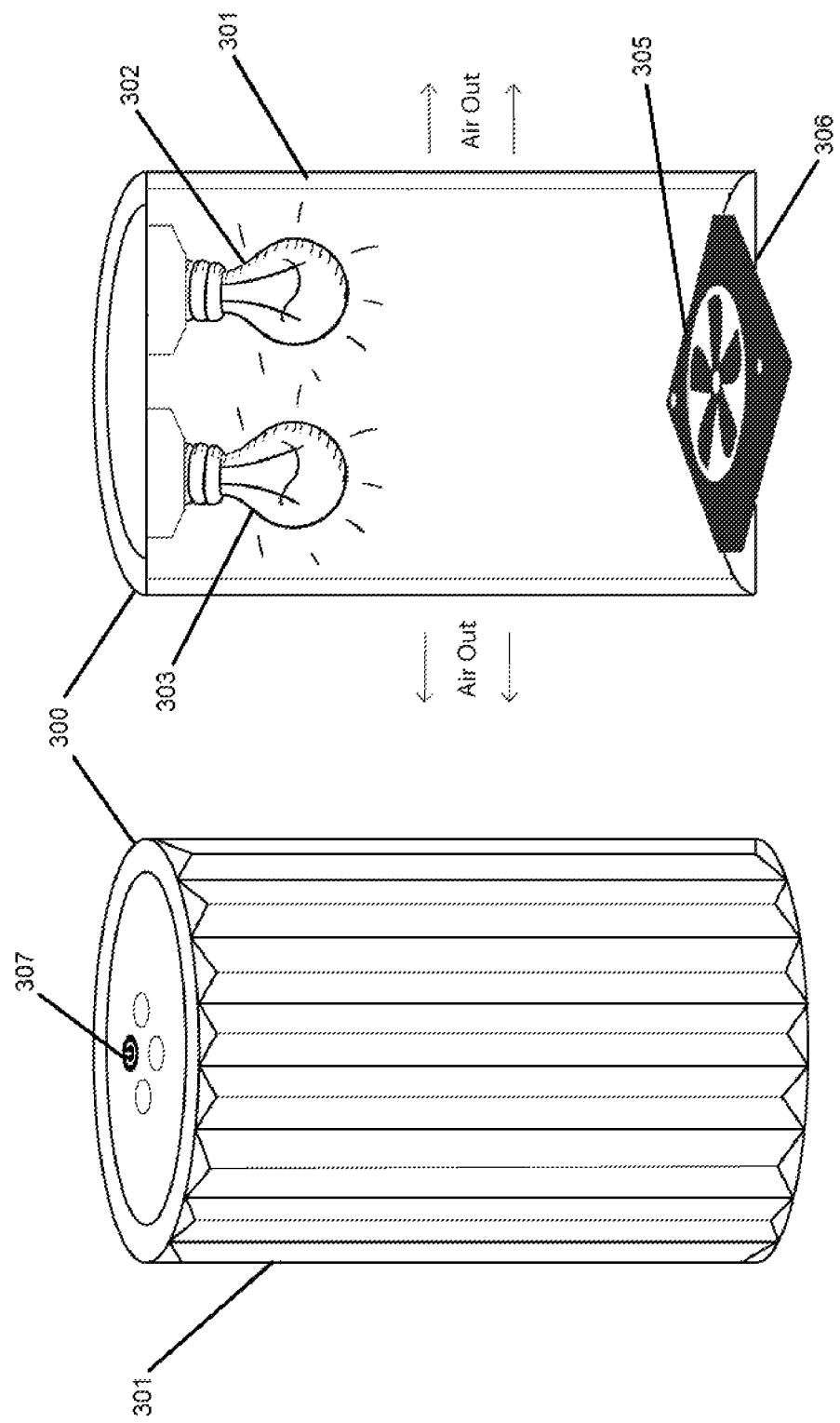
FIG. 3 schematically depicts a diagram of another anti-bacterial lighting fixture with a cylindrical housing without photocatalyst coating on the housing.

FIG. 3 is an embodiment of the lighting device of the present disclosure in a form of a cylindrical lighting fixture 300. The housing 301 houses the first light source 302, the second light source 303, and a fan 305. The fan 305 is disposed at the air inlet port 306. The translucent housing 301 is air-permeable without any an anti-bacterial photocatalyst coating. The first light source 302 is a visible light source emitting a visible light with a spectral power distribution (SPD)>95% in a visible light wavelength range (>400 nm). The second light source 303 is a far-UVC light source emitting a non-visible light with an SPD>90% in a 200 nm~230 nm wavelength range. The first light source 302 and the second light source 303 are disposed inside the housing 301. The fan 305 sucks an ambient air into the housing 301 through the air-inflow port 306, and it forces the air out through the air-permeable housing 301. The air-permeable translucent housing 301 traps airborne pathogens. The far-UVC light emitted from the second light source 303 disinfects the pathogens inside the housing whether in the air or on the surface of the housing.

The translucent housing 301 is free-standing and requires no frame to house the first light source 302, the second light source 303, and the fan 305. The primary ingredient of the anti-bacterial photocatalyst 304 is rhombus-shaped anatase-type titanium dioxide ($TiO_2$). The anti-bacterial photocatalyst 304 further include nano silver particles as the secondary photocatalytic ingredient. Though not shown explicitly in FIG. 3, the housing 301 can be removed for replacement when it becomes dirty. The housing 301 is made of non-woven fabric.

Figure 4:
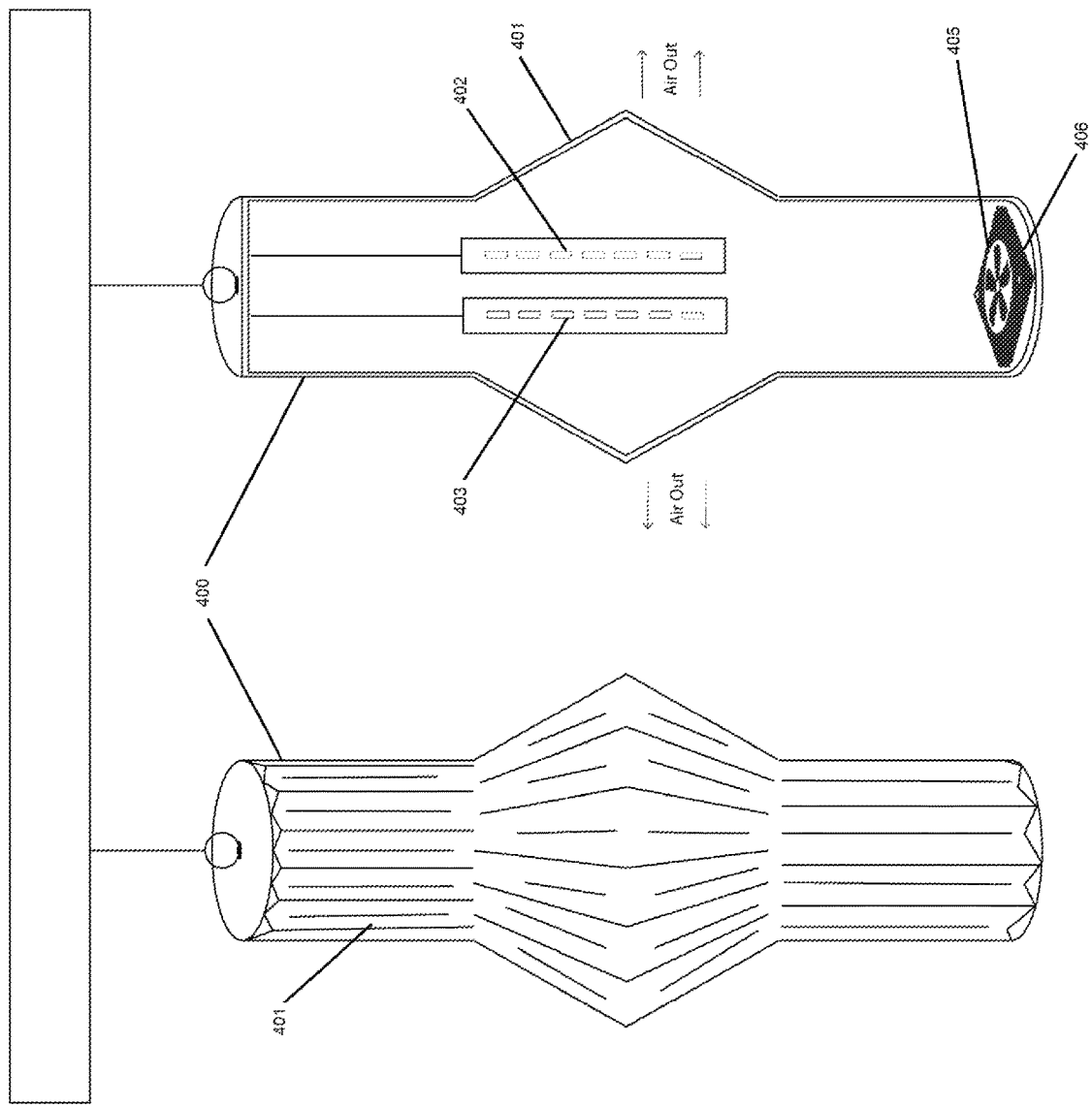
FIG. 4 schematically depicts a diagram of another anti-bacterial lantern fixture without photocatalyst coating on the housing.

FIG. 4 is an embodiment of the lighting device of the present disclosure in a form of a lantern fixture 400. The housing 401 houses the first light source 402, the second light source 403, and a fan 405. The fan 405 is disposed at the air inlet port 406. The translucent housing 401 is air-permeable and is coated with an anti-bacterial photocatalyst 404 on its surface. The first light source 402 is a visible light source, comprising multiple LEDs and emitting a visible light with a spectral power distribution (SPD)>95% in a visible light wavelength range (>400 nm). The second light source 403 is a far-UVC light source, comprising multiple LEDs and emitting a non-visible light with an SPD>90% in a 400 nm-230 nm wavelength range. Both light sources 402, 403 are disposed inside the housing 401. The fan 406 sucks an ambient air into the housing 401 through the air-inflow port 406, and it forces the air out through the air-permeable housing 401. The air-permeable translucent housing 401 traps airborne pathogens. The far-UVC light emitted from the second light source 403 disinfects the pathogens inside the housing whether in the air or on the surface of the housing. Though not shown explicitly in FIG. 4, the housing 401 can be removed for replacement when it becomes dirty.

Additional and Alternative Implementation Notes

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A lighting device, comprising
a translucent housing;
a first light source;
a second light source;
an air inflow port; and
an air circulation mechanism;
wherein:
the translucent housing houses the first light source, the second light source, and the air circulation mechanism,
the translucent housing is air-permeable, and is coated with an anti-bacterial photocatalyst on its surface,
the first light source comprises a visible light source configured to emit a visible light with a spectral power distribution (SPD)>95% in a visible light wavelength range>400 nm,
the second light source comprises a far-ultraviolet-C (UVC) light source configured to emit a non-visible light with an SPD>90% in a 200 nm~230 nm wavelength range,
the first light source and the second light source are disposed inside the housing, and their lights shine through the translucent housing to activate the anti-bacterial photocatalyst coated on the housing,
the air circulation mechanism is configured to suck an ambient air into the housing through the air-inflow port and force the air out through the air-permeable housing,
the air-permeable translucent housing is configured to trap at least a portion of airborne pathogens, and the activated anti-bacterial photocatalyst on the housing is configured to disinfect the trapped pathogens, and
the far-UVC light emitted from the second light source is configured to disinfect directly at least another portion of the airborne pathogens inside the housing and the trapped pathogens on the surface of the housing.

2. The lighting apparatus of claim 1, wherein the translucent housing is free-standing and requires no frame to house the first light source, the second light source, and the air circulation mechanism.

3. The lighting apparatus of claim 1, wherein a primary ingredient of the anti-bacterial photocatalyst is titanium dioxide ($TiO_2$).

4. The lighting apparatus of claim 3, wherein the primary ingredient is rhombus-shaped anatase-type titanium dioxide ($TiO_2$).

5. The lighting apparatus of claim 3, wherein a secondary ingredient of the anti-bacterial photocatalyst is another metal comprising silver, gold, copper, zinc, nickel, or a combination thereof.

6. The lighting apparatus of claim 1, wherein a primary ingredient of the anti-bacterial photocatalyst is a noble metal nanoparticle comprising gold (Au) or sliver (Ag).

7. The lighting apparatus of claim 1, wherein the air circulation mechanism comprises a fan.

8. The lighting apparatus of claim 1, wherein the housing is replaceable.

9. The lighting apparatus of claim 1, wherein the housing comprises a non-woven fabric.

10. The device of claim 1, wherein the first light source comprises one or more light emitting diodes (LEDs).

11. The device of claim 1, wherein the first light source comprises one or more organic light emitting diodes (OLEDs).

12. The device of claim 1, wherein the second light source comprises one or more light emitting diodes (LEDs).

13. A lighting device, comprising
a translucent housing;
a first light source;
a second light source;
an air inflow port; and
an air circulation mechanism;
wherein:
the translucent housing houses the first light source, the second light source, and the air circulation mechanism,
the translucent housing is air-permeable,
the first light source comprises a visible light source configured to emit a visible light with a spectral power distribution (SPD)>95% in a visible light wavelength range>400 nm,
the second light source comprises a far-ultraviolet-C (UVC) light source configured to emit a non-visible light with an SPD>90% in a 200 nm~230 nm wavelength range,
the first light source and the second light source are disposed inside the housing, and their lights shine through the translucent housing,
the air circulation mechanism is configured to suck an ambient air into the housing through the air-inflow port and force the air out through the air-permeable housing,
the air-permeable translucent housing is configured to trap at least a portion of airborne pathogens, and
the far-UVC light emitted from the second light source is configured to disinfect directly pathogens inside the housing whether airborne or on a surface of the translucent housing.

14. The lighting apparatus of claim 13, wherein the translucent housing is free-standing and requires no frame to house the first light source, the second light source, and the air circulation mechanism.

15. The lighting apparatus of claim 13, wherein the air circulation mechanism comprises a fan.

16. The lighting apparatus of claim 13, wherein the housing is replaceable.

17. The lighting apparatus of claim 13, wherein the housing comprises a non-woven fabric.

18. The device of claim 13, wherein the first light source comprises one or more light emitting diodes (LEDs).

19. The device of claim 13, wherein the first light source comprises one or more organic light emitting diodes (OLEDs).

20. The device of claim 13, wherein the second light source comprises one or more light emitting diodes (LEDs).

* * * * *